United States Patent [19]
Ohtomo et al.

[11] Patent Number: 5,234,427
[45] Date of Patent: Aug. 10, 1993

[54] ELECTROSURGICAL UNIT

[75] Inventors: Naoki Ohtomo; Shizuo Ninomiya, both of Mitaka; Takeshi Kobayashi, Ueda, all of Japan

[73] Assignee: Aloka, Co., Ltd., Tokyo, Japan

[21] Appl. No.: 598,231

[22] Filed: Oct. 16, 1990

[30] Foreign Application Priority Data

Oct. 18, 1989 [JP] Japan .................. 1-272194

[51] Int. Cl.$^5$ .............................. A61B 17/39
[52] U.S. Cl. ......................... 606/37; 606/42
[58] Field of Search ............... 606/34, 37–40, 606/42, 45, 49

[56] References Cited

U.S. PATENT DOCUMENTS

| 4,398,534 | 8/1963 | Hagiwara | 606/37 |
| 4,632,109 | 12/1986 | Paterson . | |
| 4,658,815 | 4/1987 | Farin et al. | 606/34 |
| 5,067,953 | 11/1991 | Feucht | 606/42 X |

FOREIGN PATENT DOCUMENTS

| 3120102 | 12/1982 | Fed. Rep. of Germany . |
| 3502193 | 7/1985 | Fed. Rep. of Germany . |
| 3627221 | 2/1988 | Fed. Rep. of Germany . |
| 2517955 | 6/1983 | France . |

Primary Examiner—Lee S. Cohen
Attorney, Agent, or Firm—Dickstein, Shapiro & Morin

[57] ABSTRACT

An electrosurgical unit for being capable of selection of desirable electrosurgical operation mode in cutting mode and coagulation mode. A handpiece for the operation is connected to a control means through an isolation means, and an operator performs the operations of cutting mode or coagulation mode by use of the handpiece. The handpiece is provided with a cutting mode switch and a coagulation mode switch. The operator can perform the mode change only in the sterile field by depression of these switches simultaneously.

11 Claims, 8 Drawing Sheets

ELECTROSURGICAL UNIT

BACKGROUND OF THE INVENTION

1. Field of the Invention

This invention relates to an electrosurgical unit and, more particularly, to an electrosurgical unit including a handpiece for surgical operations, with two switches for controlling at least two high frequency current outputs having waveforms different from each other.

2. Description of the Prior Art

There has heretofore been known an electrosurgical unit having a handpiece provided with two switches (hereinafter referred to as "one switch for cutting mode and the other switch for coagulation mode") for controlling at least two high frequency current outputs for the purpose of cutting and coagulation mode, which are different in waveform from each other. In this electrosurgical unit, the handpiece which is in the sterile field performs activation and interruption of the high frequency current outputs, while a main controller of the electrosurgical unit which is outside of the sterile field changes the operating conditions such as an output mode and a set value of the output.

Therefore, in the above-described electrosurgical unit, an operator, i.e. a surgeon performing a surgical operation by the use of the handpiece in the sterile field cannot change the output mode and the set value of the output directly as he desires and let his assistant perform the above changing operation instead of him, thus presenting such a problem that the controllability of the electrosurgical unit in the surgical operation is deteriorated.

To obviate this problem, there has been proposed an electrosurgical unit wherein two more switches for changing the operating conditions such as the output mode and the set value of the output are additionally provided on the handpiece as described in U.S. Pat. No. 4,632,109. With this improved electrosurgical unit, the surgeon performing the surgical operation in the sterile field by the use of the handpiece can directly change the output mode and the set value of the output.

This improved electrosurgical unit has had the above-described arrangement, whereby the handpiece provided with switches for transmitting a selective signal to change the operating conditions such as the output mode and the set value of the output and an additional circuit in the main controller for receiving the signal to select the operating condition in response to the selective instruction from the switches of the handpiece must be newly installed, so that there is no interchangeability with the conventional electrosurgical unit, thus presenting such a problem that the improved electrosurgical unit is uneconomical. Furthermore, due to the controllability and the installation space permitted in the handpiece, the number of the switches to be additionally provided is limited, whereby parts of the operating conditions which are changeable have been limited in number.

SUMMARY OF THE INVENTION

The present invention has been developed to obviate the above-described disadvantages and has as its object the provision of an electrosurgical unit wherein the operating conditions can be changed widely without requiring a newly designed handpiece.

The electrosurgical unit according to the present invention comprises: a high frequency output generating means for generating high frequency current outputs having at least two waveforms different from each other; a handpiece having two switches for controlling the high frequency current outputs having at least two waveforms different from each other; a set-input means for setting and inputting operating conditions; and a control means provided for receiving a combination signal from the two switches to select the operating condition of the set-input means.

Furthermore, in the present invention, the control means may select the operating condition only when the two switches are closed simultaneously.

Further, it is preferable in the present invention that there is provided a warning means which gives a notice of condition changing when the control means changes the operating condition.

Furthermore, in the present invention, the operating condition to be changed by the control means may be an operating condition of given parts previously determined.

Further, in the present invention, the operating condition to be changed by the control means may be an operating condition previously stored in a memory means provided in the control means.

Further, in the present invention, it is desirable that the memory means can be detached from the control means of the electrosurgical unit.

In the electrosurgical unit according to the present invention, at least two high frequency current outputs different in waveform from each other are produced by the high frequency output generating means, and the control means changes the operating condition of the set-input means when the control means receives the combination signal from the two switches provided on the handpiece.

DETAILED DESCRIPTION OF THE INVENTION

The preferred embodiments of the present invention will hereunder be described with reference to the accompanying drawings.

Figure 1:
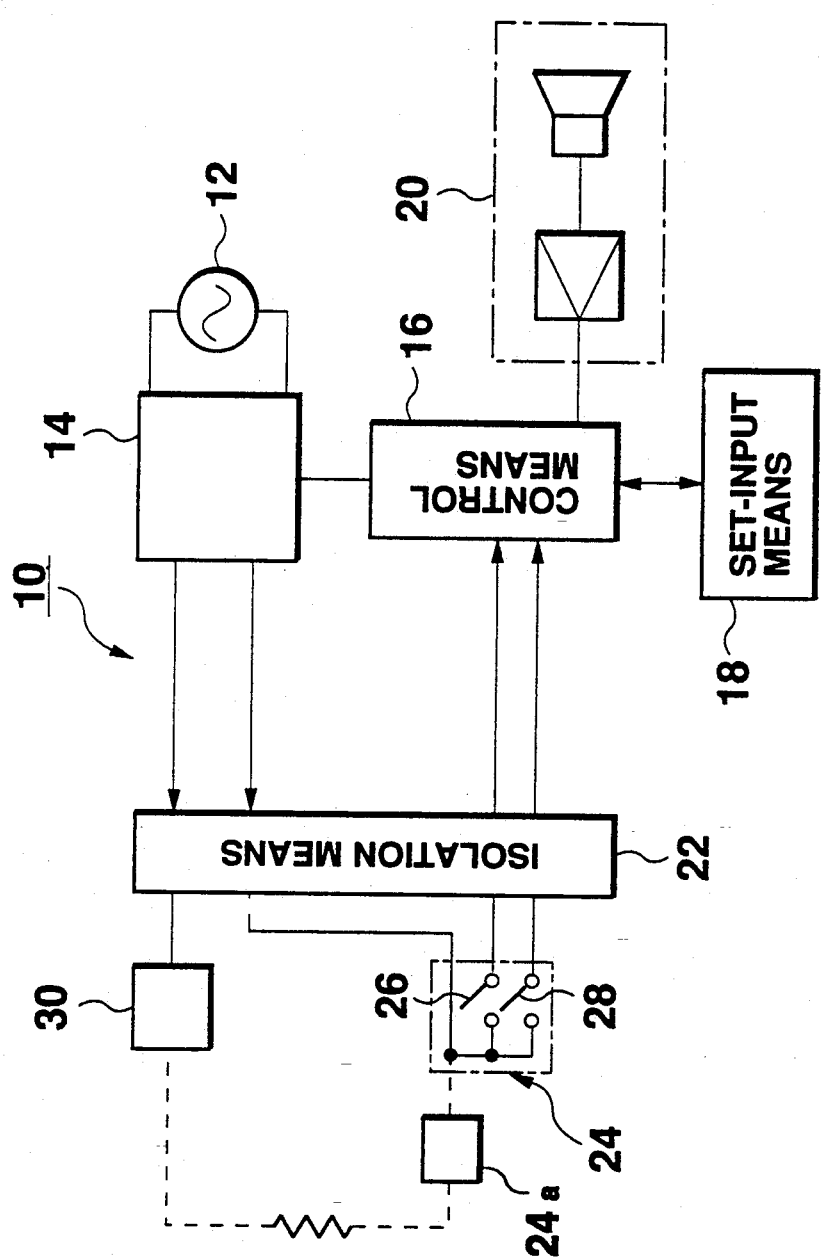
FIG. 1 is a circuit diagram showing the arrangement of a first embodiment of the electrosurgical unit according to the present invention.

FIG. 1 is a circuit diagram showing the arrangement of a first embodiment of an electrosurgical unit according to the present invention. An electrosurgical unit 10 includes a high frequency output generator 14 for which an AC power source 12 supplies AC current and a control means 16.

Figure 2:
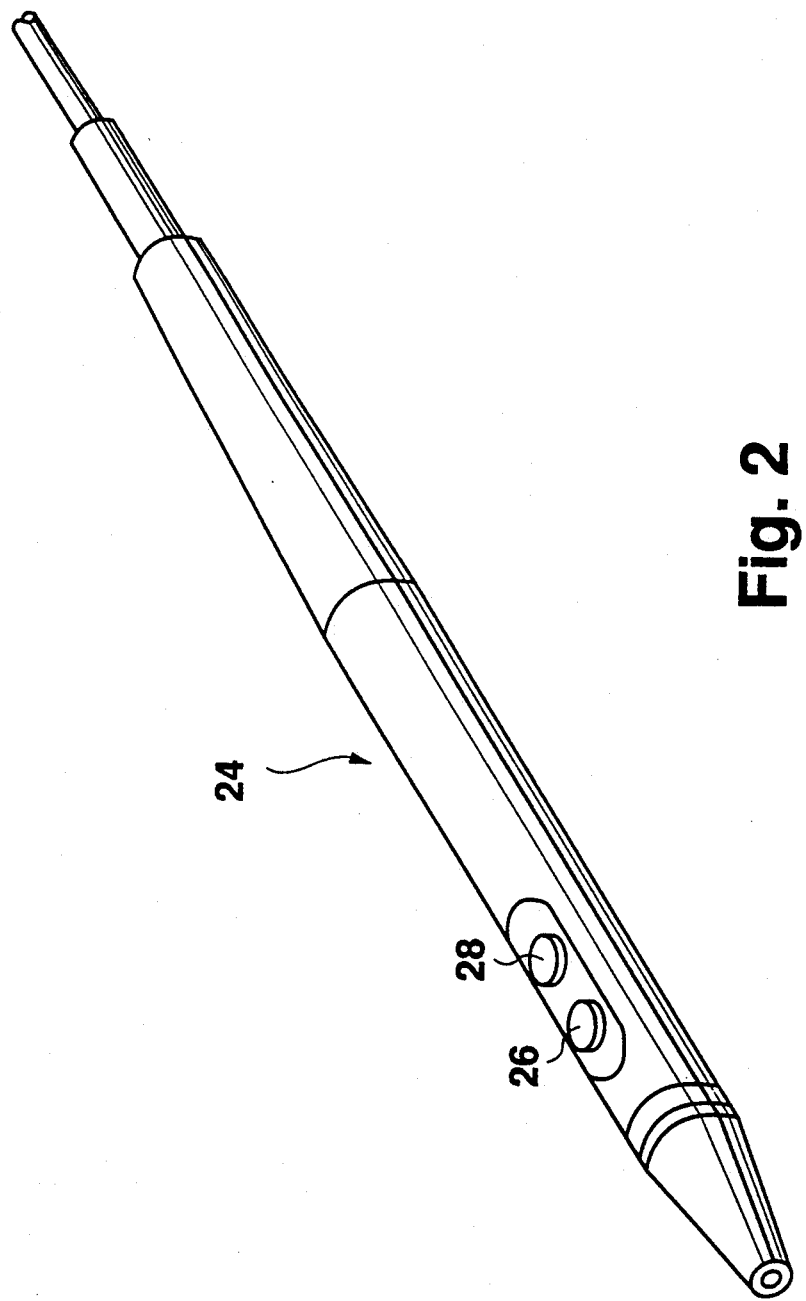
FIG. 2 is a perspective view showing the handpiece with two switches according to the present invention.

Connected to the control means 16 are the generator 14, a set-input means 18 for inputting an operating conditions, a warning device 20 for giving a notice of condition changing, and further, a cutting mode switch 26 and a coagulation mode switch 28 of a handpiece 24 through an isolation means 22 as shown in FIG. 2. Furthermore, connected to the generator 14 are an active electrode 24a of the handpiece 24 and a return electrode plate or patient plate 30 through the isolation means 22.

In this embodiment, the isolation means 22 comprises: a transformer for transforming the high frequency power of the generator 14 to the electrosurgical power supplied to the pair of electrodes 24a and 30 in isolated condition between the generator 14 and the electrodes 24a and 30, and a photo-coupler for transmitting a selective signal of switches 26, 28 to the control means 16 in also isolated condition.

Figure 3:
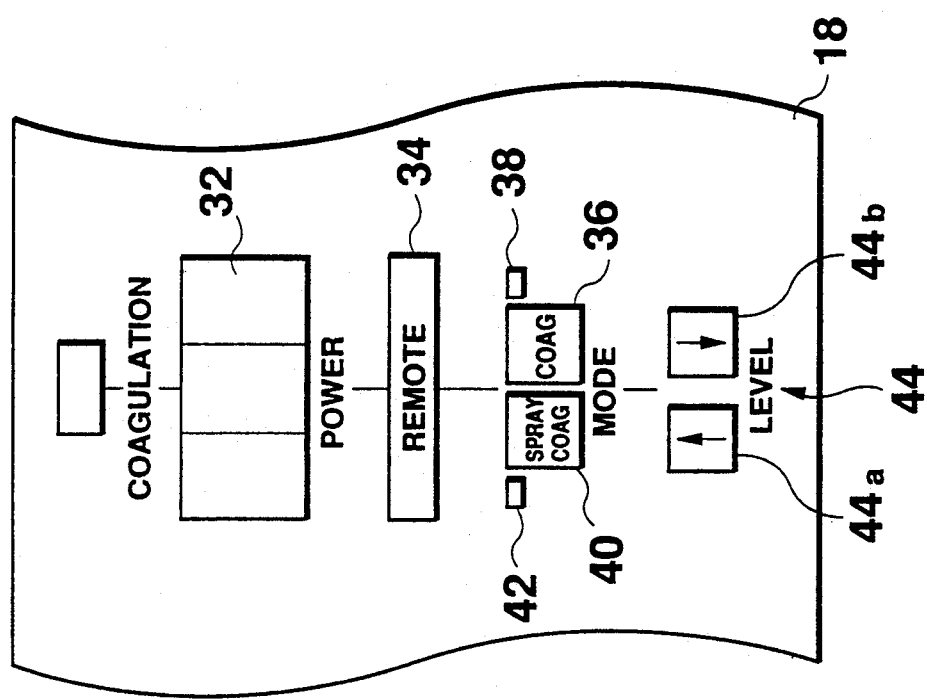
FIG. 3 is a plan view showing the set-input means according to the present invention.

As shown in FIG. 3 in detail, a portion of coagulation mode of the set-input means 18 has a output setting indicator 32 for indicating an output, and a condition change noticing indicator 34 for indicating a notice of condition changing during the process of changing operation of an operating condition by the cutting mode switch 26 and the coagulation mode switch 28 of the handpiece 24 being provided at a position adjacent the output setting indicator 32.

Furthermore, provided at positions adjacent the condition change noticing indicator 34 are a normal coagulation mode key 36 for selecting a normal coagulation mode, a normal coagulation mode indicator 38 for indicating that the normal coagulation mode key 36 is selected, a spray coagulation mode key 40 for selecting a spray coagulation mode and a spray coagulation mode indicator 42 for indicating that the spray coagulation mode key 40 is selected.

Further, provided at a position adjacent the normal coagulation mode key 36 and the spray coagulation mode key 40 are output set keys 44 including a level increasing key 44a and a level decreasing key 44b.

The structure of the first embodiment of the present invention has now been fully described in the above description. Thus the function of this embodiment will hereunder be described.

When a cutting mode is performed by the use of the electrosurgical unit 10, if the surgeon turns on the cutting mode switch 26 of the handpiece 24, then an on-signal from the cutting mode switch 26 is transmitted to the control means 16 through the isolation means 22.

Then, upon receiving the on-signal from the cutting mode switch 26, the control means 16 gives an instruction to the generator 14 so as to output a high frequency current output suitable for cutting mode.

Upon receiving the instruction signal from the control means 16, the generator 14 outputs the high frequency current output having a waveform suitable for cutting mode to the active electrode 24a of the handpiece 24 through the isolation means 22.

Furthermore, when a coagulation mode is performed, if the coagulation mode switch 28 is turned on, then the generator 14 outputs a high frequency current output having a waveform suitable for coagulation mode to the active electrode 24a of the handpiece 24 through the isolation means 22.

On the other hand, when the cutting mode switch 26 and the coagulation mode switch 28 are turned on simultaneously to change an operating condition, an output mode for example, upon receiving a couple of on-signals from the cutting mode switch 24 and the coagulation mode switch 28, the control means 16 changes the mode to a predetermined operating condition. For example, the mode is changed from the normal coagulation mode to the spray coagulation mode, the normal coagulation mode indicator 38 is turned off, and the condition change noticing indicator 34 and the spray coagulation mode indicator 42 are turned on.

In the preferred embodiment, only when the cutting mode switch 26 and the coagulation mode switch 28 are turned on within a predetermined time period ($t_1 = 0.3$ sec), the control means 16 is set to perform the control to change the operating condition, therefore such a mistaken changing can be avoided that, while the high frequency current output is being generated due to the continuous depression of one of the switches, the other of the switches is momentarily depressed later mistakenly. Further, only when the cutting mode switch 26 and the coagulation mode switch 28 are turned on over a predetermined time period ($t_2 = 1$ sec), respectively, the control means 16 is set to perform the control to change the operating condition, then a mistaken operation without intention of the surgeon can be avoided.

Further, when generating of the high frequency current output is delayed from the on-operation of the cutting mode switch 26 or the coagulation mode switch 28 for a time period equal to or slightly longer than the aforesaid 0.3 sec ($t_1$), an unnecessary generating of the high frequency current output due to a small difference of time between the successive depression of both the cutting mode switch 26 and the coagulation mode switch 28 by the surgeon can be reliably avoided.

Further, when the operating condition is changed, if a notice sound is given by the warning device 20 only for a predetermined time period ($t_3 = 0.5$ sec) in the control means 16, then the surgeon can confirm the change in the operating condition more easily and the alarm sound can be given to an unintended change in the operating condition.

Figure 4:
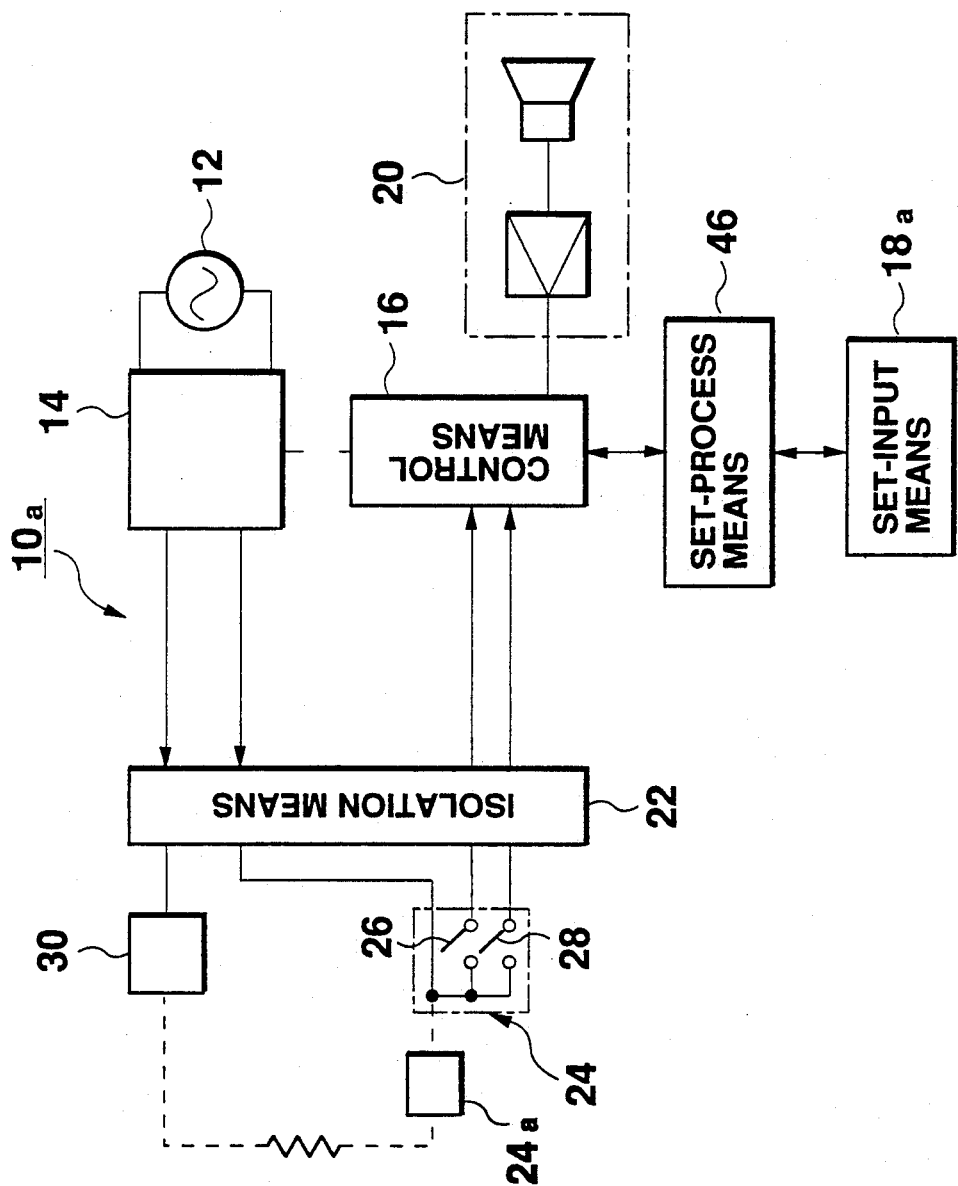
FIG. 4 is a circuit diagram showing the arrangement of a second embodiment of the electrosurgical unit according to the present invention.

The second embodiment of the present invention which is selecting some one of a plurality of operating conditions will hereunder be described with reference to FIGS. 4 and 5. Additionally, reference numerals in the above first embodiment are applied to designate same or similar elements to ones in this embodiment, in order to make easier the description of the embodiment.

In an electrosurgical unit 10a, between the control means 16 and a set-input means 18a, there is provided a set-process means 46 performing selections and processes of a plurality of operating conditions, for example, a high frequency output mode and an output value of cutting mode, and a high frequency output mode and an output value of coagulation mode.

The set-input means 18a is provided with an output set indicator 48 for indicating an output of cutting mode. Provided at positions adjacent the output set indicator 48 are four selection keys 50 for each selecting an output mode and an output mode indicator 52 for indicating what keys 50 are selected.

Further, provided at a position adjacent the four selection keys 50 is an output set keys 54 including a level increasing key 54a and a level decreasing key 54b.

Furthermore, provided at a position adjacent the condition change noticing indicator 34 is a first mode indicator 56 for instructing what part is to be selected out of a plurality of operating conditions. Provided at a position adjacent the first mode indicator 56 is a second mode indicator 58 for instructing a change of a content of the selected operating condition. Adjacent the second mode indicator 58, there is provided an end indicator 60 for indicating the end of a change of the operating condition. Function of this embodiment will hereunder be described.

When the cutting mode switch 26 and the coagulation mode switch 28 are turned on simultaneously to change the operating condition, upon receiving the on-signals from the cutting mode switch 26 and the coagulation mode switch 28, respectively, the control means 16 instructs a process of a change of the operating conditions, for example, a high frequency output mode and an output value of cutting mode, and a high frequency output mode and an output value of coagulation mode and further gives a notice sound through the warning device 20.

Then, the set-process means 46 turns on the condition change noticing indicator 34 of the set-input means 18, and both the set-process means 46 and the control means 16 are set at a first mode for instructing what part out of a plurality of operating conditions is to be selected.

In the case where the surgeon continues to turn on the cutting mode switch 26 and the coagulation mode switch 28, upon receiving the on-signals from the cutting mode switch 26 and the coagulation mode switch 28, the control means 16 utilizes the set-process means 46 for turning on or off the output set indicator 48, the output mode indicator 52, the output set indicator 32, the normal coagulation mode indicator 38 and the spray coagulation mode indicator 42 in a predetermined order, and turns on the first mode indicator 56 so as to instruct it to select a desired operating condition.

Subsequently, in such a desirable operating condition that the output set indicator 32 repeats turning on and off, for example, if both the cutting mode switch 26 and the coagulation mode switches 28 are turned off, then setting of the first mode is completed, and the control means 16 and the set-process means 46 are set at the second mode where a selected operating condition, i.e. the output of coagulation mode is changed.

Further, the set-process means 46 turns on the second mode indicator 58 so as to instruct it to change the content of a desirable operating condition, i.e. the output of coagulation mode.

In this case, the cutting mode switch 26 functions as a level increasing key for increasing the output level of coagulation mode, and the coagulation mode switch 28 functions as a level decreasing key for decreasing the output level of coagulation mode.

Then, the output of coagulation mode is set at a desirable value by the cutting mode switch 26 and the coagulation mode switch 28, and when the cutting mode switch 26 and the coagulation mode switch 28 are turned on again, upon receiving the on-signals from the cutting mode switch 26 and the coagulation mode switch 28, the control means 16 and the set-process means 46 release the second mode, and the set-process means 46 turns on a condition change end indicator 60 for indicating the end of process of a change in the operating condition for a predetermined time period.

Thereafter, the control means 16 interrupts the warning device 20 in operation and returns to the normal operating condition.

Further, the third embodiment of the present invention which is selecting some one out of the plurality of the operating conditions will hereunder be described with reference to FIG. 6. The arrangement of this embodiment is similar to that illustrated in FIG. 4, so that the description of its structure will be omitted.

Figure 5:
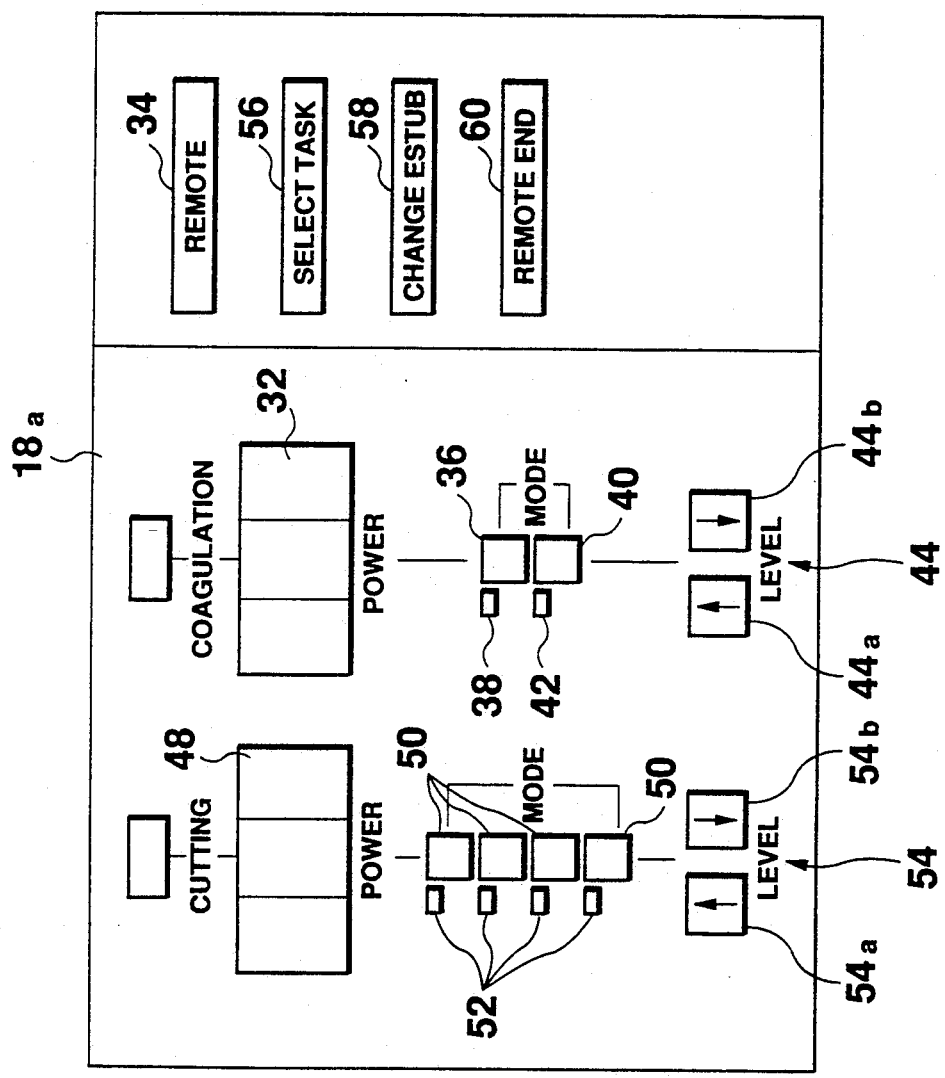
FIG. 5 is a plan view showing the set-input means of the second embodiment according to the present invention.
Figure 6:
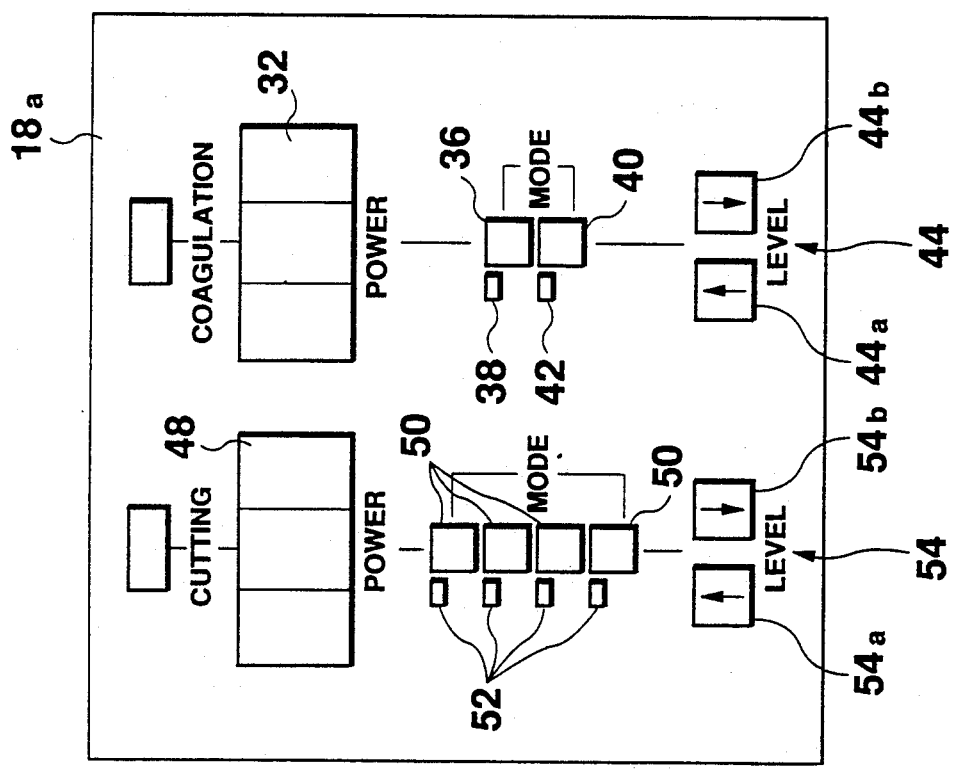
FIG. 6 is a plan view showing an example of the set-input means of a third embodiment of the electrosurgical unit according to the present invention.

The arrangement of FIG. 6 is dispensed with the indicators 34, 56, 58 and 60 as shown in the arrangement of FIG. 5, so that the structure will be understood clearly without detailed description.

Function of this embodiment will hereunder be described.

When the cutting mode switch 26 and the coagulation mode switch 28 are turned on simultaneously to change the operating condition, upon receiving the on-signals from the cutting mode switch 26 and the coagulation mode switch 28, the control means 16 instructs the set-process means 46 to change the operating conditions, for example the high frequency current output mode and the output value of cutting mode, and the high frequency current output mode and the output value of coagulation mode, and gives the notice sound through the warning device 20.

Then, the set-process means 46 makes the cutting output mode indicator 52 of the set-input means 18a flicker.

Here, the surgeon turns off the cutting mode switch 26 and the coagulation mode switch 28.

When the coagulation mode switch 28 is turned on in this condition, the set-process means 46 instructs a change in the cutting output mode, switches the cutting output modes in a predetermined order, causes to raise the notice sound, and the output mode indicator 52 of the set-input means 18a is switched to the succeeding change in the operating condition.

At this time, the set-process means 46 indicates an output set value and an "UP" message for example, on the cutting output set indicator 48 periodically.

By this display or notice, the surgeon is urged to perform a process of increasing the output set value of cutting mode.

When the coagulation mode switch 28 is turned on in this condition, the set-process means 46 instructs an increase in a cutting output set value, and subsequently increases the set value only by a predetermined value. The above operation further causes to raise the notice of condition changing and makes to change an indication on the cutting output set indicator 48 of the set-input means 18a.

Subsequently, when the cutting switch 26 is depressed, the set-process means 46 moves to a process of a change of decreasing the cutting output set value as being a change of the succeeding operating condition. At this time, the set-process means 46 indicates an output set value and a "DOWN" message for example, on the cutting output set indicator 48 of the set-input means 18a periodically.

By this display or notice, the surgeon is urged to perform a process of decreasing an output set value of cutting mode.

When the coagulation mode switch 28 is turned on in this condition, the set-process means 46 instructs a decrease in the cutting output set value to decrease the set value only by a predetermined value, causes to raise the condition changing notice, and changes the indication of the cutting output set indicator 48 of the set-input means 18a.

When the cutting mode switch 26 is depressed similarly as described above, the process moves from a process of a change of the coagulation output mode to a process of increasing the coagulation output, and further to a process of decreasing the coagulation output, and, if the coagulation mode switch 28 is depressed during anywhere of the aforesaid processes, the operating condition can be changed. Thereafter, if the cutting mode switch 26 is turned on again, then the notice sound is given, and the normal operating condition is restored simultaneously with the termination of the notice sound Another operation can be obtained by selecting some one of the plurality of operating conditions according to the third embodiment.

Function thereof will hereunder be described with reference to FIG. 4.

When the cutting mode switch 26 and the coagulation mode switch 28 are turned on simultaneously to change the operating condition, upon receiving the on-signals from the cutting mode switch 26 and the coagulation mode switch 28, the control means 16 gives an instruction to the set-process means 46 so as to perform a change in the operating condition and raises the notice sound through the warning device 20. At this time, setting of the operating condition which is changeable will be restricted to the cutting mode or the coagulation mode. This restriction is determined depending upon that which switch is depressed previously, the cutting mode switch 26 or the coagulation mode switch 28.

When the switch depressed previously is the cutting mode switch 26, this fact is stored by the set-process means 46, and, in this case, the changeable operating condition is restricted to the high frequency current output mode and the output value of cutting mode. By this restriction, the number of a series of operations can be significantly decreased, so that the controllability of the electrosurgical unit can be improved. Further, in selecting of the operating conditions, when the selection is made in an order of "mode change", "output value up" and "output value down", the set-process means 46 stores the fact that what the surgeon made a change previously, and this fact is necessarily presented first as a selected item from the preceding items of change, whereby the operating condition which is probably desired by the surgeon in a highest priority at present is presented first of all, thereby generally being capable of improvement of the controllability.

Figure 7:
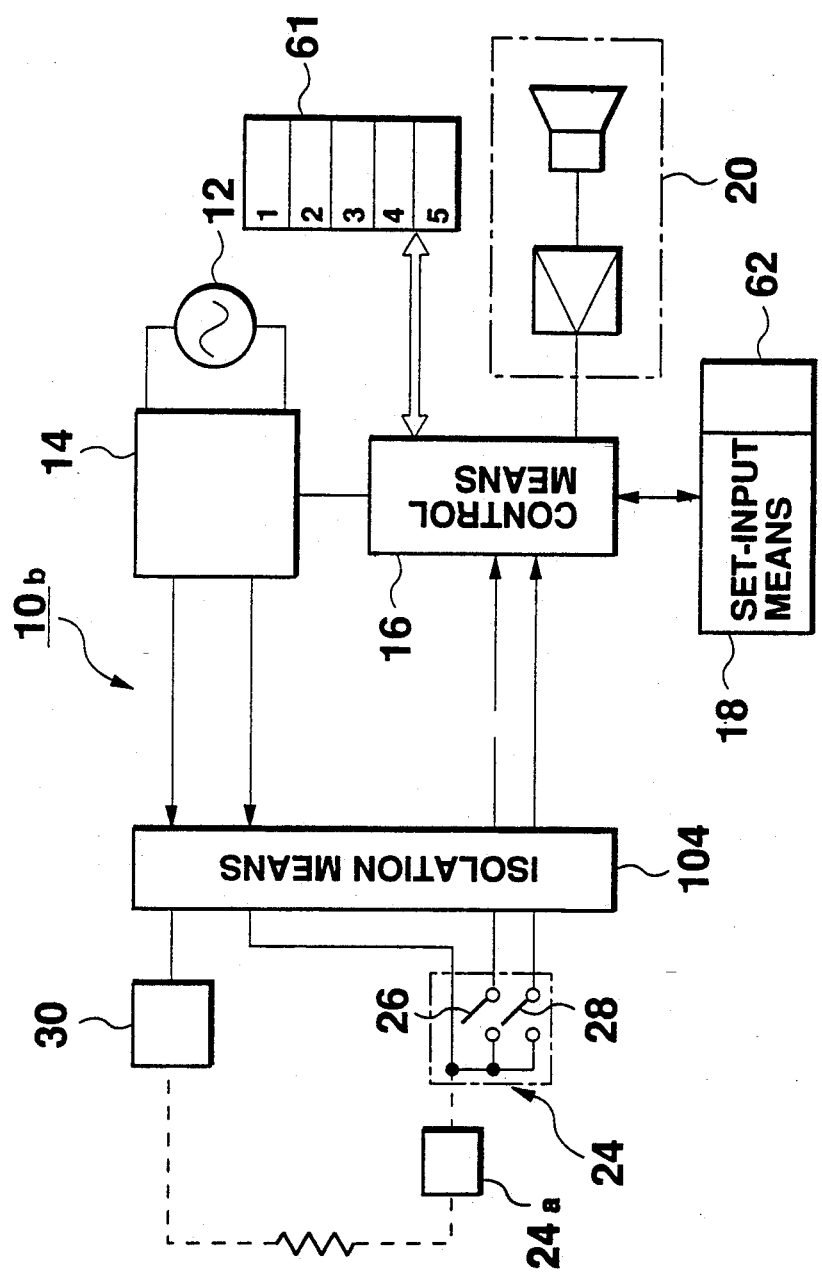
FIG. 7 is a circuit diagram showing the arrangement of a fourth embodiment of the electrosurgical unit according to the present invention.
Figure 8:
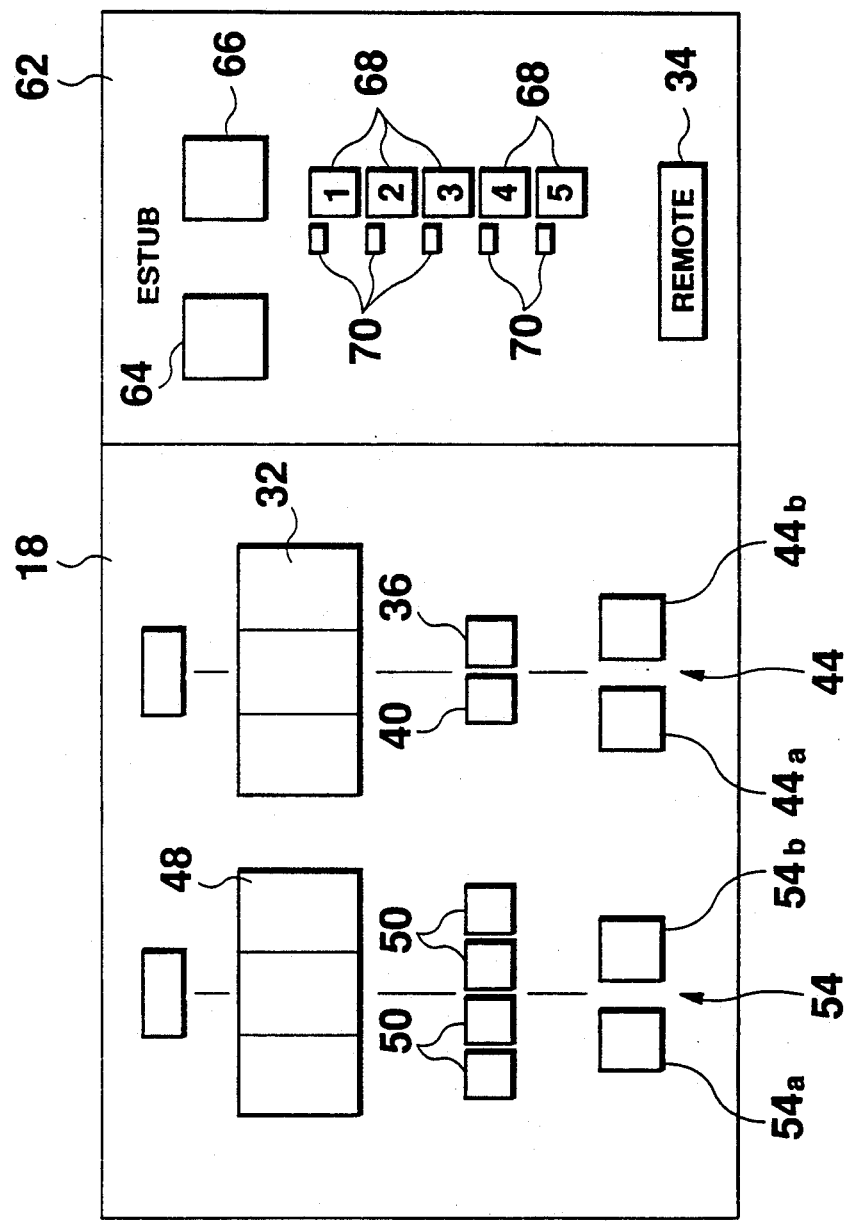
FIG. 8 is a plan view showing the set-input means of the fourth embodiment according to the present invention.

The fourth embodiment having a memory means will hereunder be described with reference to FIGS. 7 and 8. Additionally, reference numerals in the aforementioned embodiments denote the same or similar elements in this embodiment, so that the detailed description will be omitted.

An electrosurgical unit 10b has a memory means 61 connected to the control means 16. The memory means 61 is to store a plurality of operating conditions.

Furthermore, read/write means 62 for writing a plurality of operating conditions in the memory means 61 and reading out a desirable operating condition stored therein is additionally provided in the set-input means 18.

Then, the read/write means 62 is provided with a read-out mode specifying key 64 for specifying a read-out mode and a write-in mode specifying key 66 for specifying a write-in mode.

Furthermore, provided at positions adjacent these keys 64 and 66, five set specifying keys 68 indicated by numerals "1", "2", "3", "4" and "5" and five set read-out specifying indicators 70 for indicating that which set specifying key 68 is selected.

Function of this embodiment will hereunder be described.

When the operating condition is stored in the memory means 61, the operating condition is set by the set-input means 18, and, after the write-in mode specifying key 66 is depressed, one of the set specifying keys 68, e.g. the "3" set specifying key 68 is depressed. As a result of this, the operating condition set at the set-input means 18 at present is stored in a memory segment address of the memory means 61 corresponding to the "3" set specifying key 68. By operations similar to the above, the respective operating conditions are stored in a memory segment address of the memory means 61 corresponding to the other set specifying keys 68.

When the surgeon turns on the cutting mode switch 26 and the coagulation mode switch 28, upon receiving the on-signals from the cutting mode switch 26 and the coagulation mode switch 28, the control means 16 turns on the condition change noticing indicator 34, and gives a notice that the operating condition is being set through the warning device 20.

Then, during the on-state where the cutting mode switch 26 and the coagulation mode switch 28 are closed, the set read-out specifying indicators 70 are turned on in a predetermined order, and the control means 16 reads out the operating conditions stored in the address segment of the memory means 61 corresponding to the set read-out specifying indicators 70 which are turned on and indicates the operating conditions on the respective indicators of the set-input means 18.

When a desirable operating condition is indicated, the surgeon turns off the cutting mode switch 26 and the coagulation mode switch 28 and selects the desirable operating condition.

Upon receiving off-signals from the cutting mode switch 26 and the coagulation mode switch 28, the control means 16 turns off the condition change noticing indicator 34 and terminates raising the notice sound through the warning device 20.

By this sequence, the electrosurgical unit 10b is brought into a usable condition.

Incidentally, the electrosurgical units 10b may be commonly utilized in many branches of speciality in hospitals. However, since the operating conditions in these branches are widely varied, if the memory means 61 is formed of IC cards, etc. which can be taken out from the main controller of the unit, then the task required for setting the operating condition can be reduced and the erasing of a plurality of accustomed operating conditions from the memory means 61 can be avoided so as to read out a desirable operating condition with ease.

Furthermore, according to the present invention, a predetermined priority in order is previously set during the time between the operation of changing the operating condition instructed by the handpiece 24 and the changing and inputting of the operating condition performed by the set-input means 18a, so that the controllability of the electrosurgical unit as a whole can be improved for the convenience of the surgeon.

Further, in the electrosurgical unit which can be provided with two or more handpieces, a predetermined priority in order is given with respect to changes in the operating condition between the plurality of handpieces, so that the general controllability can be improved.

As has been described hereinabove, according to the present invention, such an arrangement is adopted that the combination signal is received from the two switches provided on the handpiece to change the operating condition, so that the operating condition can be changed widely without requiring a newly designed handpiece.

Furthermore, the operating condition can be changed only when the two switches are closed simultaneously, so that a change in the operating condition due to the mistaken operation can be eliminated.

Further, the changing notice is given by the warning device when the operating condition is changed, so that the process of a change in the operating condition can be reliably informed.

The operating condition to be changed is the operating condition previously stored in the memory means, so that the operating condition can be set easily.

Furthermore, the memory means can be taken out from the main controller of the unit, so that the desirable operating condition can be read out easily, avoiding erasing of the plurality of accustomed operating conditions from the memory means.

What is claimed is:

1. An electrosurgical unit comprising:
   high frequency output generating means for generating a high frequency cutting mode current output and a high frequency coagulation mode current output, said cutting mode current output having a first waveform and said coagulation mode current output having a second waveform, said first and second waveforms being different from each other;
   set-input means for setting and inputting operating conditions for said high frequency output generating means;
   control means for selecting an operating condition from said set-input means and for controlling said high frequency output generating means in accordance with said operating condition; and
   a handpiece having first and second switches for transmitting signals to said control means;
   said control means being arranged such that said high frequency cutting mode current output is generated by said high frequency output generating means when said first switch is closed and said second switch is open, and such that said coagulation mode current output is generated by said generating means when said second switch is closed and said first switch is open; and said control means being further arranged such that said operating condition is changed when said first and second switches are closed simultaneously; and wherein said high frequency output generating means is not operated when said first and second switches are closed at the same time; and
   wherein said set-input means includes an indicator for indicating a mode of operation when said operating condition is changed.

2. The electrosurgical unit as set forth in claim 1, wherein said control means is arranged such that the operating condition is changed only when said two switches are closed simultaneously and continue to be closed over a predetermined time period.

3. The electrosurgical unit as set forth in claim 2, wherein said means includes means for measuring said time period.

4. The electrosurgical unit as set forth in claim 1, further comprising means for measuring a small difference of time between successive depressions of said switches to determine the case where said switches are closed substantially at the same time.

5. The electrosurgical unit as set forth in claim 4, wherein said control means includes means for delaying generation of an output.

6. The electrosurgical unit as set forth in claim 1, wherein there is provided a warning means for giving a condition changing notice when the operating condition is changed.

7. The electrosurgical unit as set forth in claim 1, wherein said unit includes means for selecting a preferred operating condition from a plurality of operating conditions in accordance with previous operation of the switches.

8. The electrosurgical unit as set forth in claim 1, further comprising a memory means for storing operating conditions for said control means.

9. The electrosurgical unit as set forth in claim 8, wherein said memory means can be detached from said control means.

10. The electrosurgical unit as set forth in claim 1, wherein said unit includes means for setting a priority in order between an operating condition changing signal from said set-input means and an operating condition changing signal generated by closing both of said switches.

11. The electrosurgical unit as set forth in claim 1, wherein said unit is provided with a plurality of handpieces, and wherein said unit includes means for providing a priority in order between inputs of combination signals from said handpiece.

* * * * *